United States Patent [19]

Leise, Jr.

[11] Patent Number: 5,401,264

[45] Date of Patent: Mar. 28, 1995

[54] OSTOMY POUCH WITH INTERNAL SQUEEZE-TO-OPEN VENT VALVE

[75] Inventor: Walter F. Leise, Jr., Lindenhurst, Ill.

[73] Assignee: Hollister Incorporated, Libertyville, Ill.

[21] Appl. No.: 229,019

[22] Filed: Apr. 18, 1994

[51] Int. Cl.⁶ ............................................. A61F 5/44
[52] U.S. Cl. ................................................. 604/333
[58] Field of Search ............... 604/333, 334; 55/385.4, 55/DIG. 12, DIG. 13

[56] References Cited

U.S. PATENT DOCUMENTS 4,203,445  5/1980  Jessup et al. ........................ 604/333
4,911,699  3/1990  Fenton ................................ 604/333

Primary Examiner—Jerome L. Kruter
Attorney, Agent, or Firm—Tilton Fallon Lungmus

[57] ABSTRACT

An ostomy pouch is provided with a normally-closed vent valve in the form of a slit-providing flexible dome secured to the interior surface of the pouch wall over a vent opening in that wall. An odor-absorbing filter extends across the vent opening (either within the dome or externally of the pouch) to deodorize gases when they are vented from the pouch. The edges of the slit seal against each other to prevent the escape of gases and protect the filter from effluent contact when the dome is in its normal unflexed state but, when the dome is squeezed between the fingers in a prescribed manner, the slit opens to permit the venting of gases from the pouch.

19 Claims, 1 Drawing Sheet

OSTOMY POUCH WITH INTERNAL SQUEEZE-TO-OPEN VENT VALVE

BACKGROUND AND SUMMARY

This invention relates to ostomy pouches having vent openings and, in particular, to pouches having both vent openings and deodorizing filters with means for sealing the vent openings until such time as it is desired to vent gases from the pouch.

It is known in the art to provide ostomy appliances having vents that are normally closed but may be opened when users wish to allow flatus to escape from and thereby deflate such pouches. For example, U.S. Pat. No. 3,759,260 discloses an ostomy pouch having a vent opening that is normally sealed by a panel, flap or tab adhesively secured to the outer surface of the pouch over the opening. When deflation of the pouch is desired, the adhesive seal is broken and, after such venting has occurred, the vent is resealed. The effectiveness of the resealing depends on the security of adhesive reattachment; if adhesion is lacking because of moisture or other causes, subsequent leakage of gases and liquids may result.

It is also known to provide pouches with continuously-open vents equipped with porous filters having absorbent materials, such as finely-divided activated carbon, capable of deodorizing gases. The aforementioned U.S. Pat. No. 3,759,260 also discloses such a filter in the form of a fibrous disc located within a pouch over a vent opening, the surface of the disc facing into the pouch being covered by an impervious panel so that gases escaping from the pouch must travel along a labyrinthine path in generally radial directions between the periphery of the filter and the vent opening. If such a filter were instead located on the outside of the pouch, then the operation would be essentially the same but the direction of radial flow through the filter would be reversed. In either case, such a filter is accessible to fluids and solids collected by the pouch, especially when the wearer is reclining or has assumed a position other than standing. Contact between the pouch's liquid/solid contents and the filter may clog such a filter and reduce or destroy its gas-filtering capability.

U.S. Pat. No. 4,203,445 discloses an ostomy appliance in which a deodorizing filter unit is mounted within a pouch adjacent the vent opening of that pouch. The filter unit is multi-layered, being composed of a fibrous core layer containing activated carbon and protective covering layers 19 and 20. Both of the covering layers are gas-transmissible but liquid impervious. While the cover layers may prevent direct contact between the fibrous filter and liquid, such cover layers (especially the inner layer 19) may themselves become obstructed in use and therefore interfere with the gas filtering-/deodorizing/ venting action that the unit is designed to provide.

Other patents representative of the state of the art are U.S. Pat. Nos. 5,250,042 and 4,449,970.

An important aspect of this invention lies in providing an ostomy pouch having a vent opening, preferably one associated with a deodorizing filter element, which is inaccessible to the contents of the pouch and which is inoperative in venting gases from the pouch until such time as the wearer squeezes the pouch in the vicinity of the vent to open a normally-closed protective valve located within the pouch.

The valve takes the form of a flexible plastic dome secured to the interior surface of a pouch wall over the vent opening in that wall. A linear slit is provided in the dome with the edges of the slit normally sealing against each other to prevent the passage of gases, liquids and solids. In a preferred embodiment of the invention, an odor-absorbing filter extends across the vent opening, either along the inner surface of the pouch wall within the dome or along the outer surface of the pouch wall over and about the vent opening. Because the dome functions as a normally-closed valve, venting of the pouch does not occur until such time as such valve is opened. Opening is achieved simply by squeezing the dome between the fingers in directions extending inwardly from generally opposite ends of the slit, causing the edges of the slit to buckle and allowing gases to exit through the valve opening. The squeezing force is applied externally of the pouch—that is, the thin, flexible wall of the pouch in the vicinity of the dome is squeezed in a manner that deforms the dome and spreads the edges of the slit. Because of shape-recovering elastic memory of the polymeric material from which the dome is formed, the opening closes as soon as the squeezing force is discontinued and the protective function of the dome is restored.

The dome may be generally circular or rectangular in outline. Its linear slit preferably extends in either a generally vertical or generally horizontal direction when the pouch is worn. Since ostomy pouches are customarily elongate in a vertical direction, the slit is therefore preferably oriented either longitudinally or transversely to the direction of pouch elongation. To open the protective valve and vent a pouch, a user need only squeeze the dome between the thumb and index finger with the thumb exerting force from one end of the slit and the index finger exerting force from the opposite end.

Other features, objects, and advantages of the invention will become apparent from the specification and drawings.

DRAWINGS

DETAILED DESCRIPTION OF PREFERRED EMBODIMENTS

Figure 1:
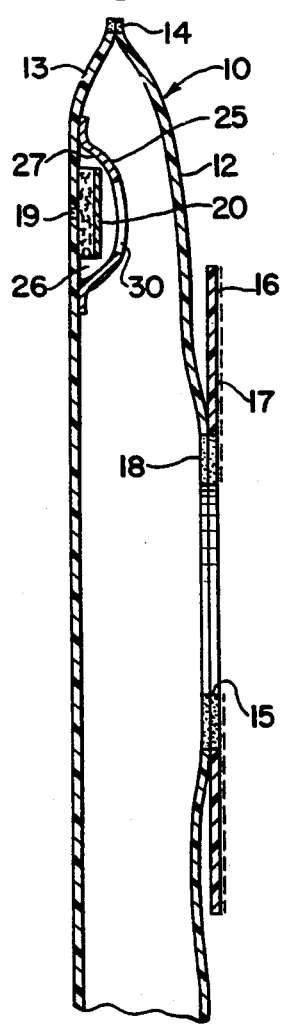
FIG. 1 is a partial vertical sectional view of an ostomy pouch having an internal squeeze-to-open vent valve of this invention.

Referring to the embodiment depicted in FIGS. 1–4, the numeral 10 generally designates an ostomy pouch having thin, flexible side walls 12 and 13 joined together at their edges as by heat seal 14. One wall 12 of the pouch is provided with a stoma-receiving opening 15, and adhesive attachment means in the form of a flexible faceplate 16 with a pressure-sensitive adhesive coating 17 are provided for securing the faceplate to the peristomal skin surfaces of a patient. In the illustration given, the ostomy appliance is what is commonly known as a one-piece appliance with the annular faceplate 16 permanently secured to the pouch about stoma opening 15 by means of heat seal 18. It is to be understood, however, that the appliance may instead be a two-piece appliance with the faceplate and pouch being separable components joined to each other by adhesive or mechanical coupling means. Since one-piece and two-piece ostomy appliances are well known in the art, further detailed description of their construction is believed unnecessary herein.

One of the pouch walls, wall 13 in the illustrated embodiment, is provided with a vent opening 19. A deodorizing gas filter 20 is secured to the pouch wall over and about that opening for purposes of deodorizing gases as they are vented from the pouch. In the embodiment of FIGS. 1–4, the filter is generally rectangular (square) in shape with rounded corners and is secured to the inside surface of wall 13 over and about vent opening 19. The filter is relatively flat and includes a porous pad 21 of fibrous material coated or impregnated with finely-divided activated carbon having a high capacity for adsorbing gaseous odors. In the illustration, the filter 20 is of the radial-flow type in common use and disclosed, for example, in aforementioned U.S. Pat. No. 3,759,260. A fluid/gas impervious coversheet 22 extends over that surface of the fibrous pad that faces into the interior of the pouch, and the opposite or outwardly-facing surface of the pad is secured, as by adhesive means 23, to the inside surface of pouch wall 13 about vent opening 19. To reach the vent opening and escape from the pouch, gases must therefore travel radially inwardly from the exposed periphery of filter pad 21 to the centrally-located vent opening 19 but, because of the fibrous character of the pad, the flow paths are labyrinthine and insure substantial interchange between the odor-absorbing agent (activated carbon) and the gases. In referring to the pad, the term "fibrous" is used here to indicate the general porous network of filaments from which the pad is formed, but it is to be understood that such fibers may also be the filaments of an open-cell polymeric foam network.

Although the deodorizing filter 20 should be flat, fibrous, and contain a deodorizing agent, it is not essential that cover layer 22 be imperforate. If the cover layer is gas-transmissible, then the flow of gases through the filter may be in generally axial directions as well as radial directions. Reference may be had to U.S. Pat. No. 4,203,445 for further details concerning such a filter. In any event, the filter must have gas-transmissible peripheral and/or planar surfaces if the filter is to perform its function in transmitting and deodorizing gases during a venting procedure. If the liquid or solid contents of pouch 10 invade such filter surfaces, the gas pathways may become obstructed and render the filter inoperative.

A flexible, shape-recovering plastic dome 25 is located within the pouch and is heat sealed or otherwise permanently secured to the inner surface of pouch wall 13 about vent opening 19. The dome also serves as a cover for filter 20 and, as shown in FIG. 1, has a chamber or cavity 26 that is large enough to accommodate filter 20 and to provide substantial spacing between the inner surface 27 of the dome and the filter when the dome is in its relaxed or undeformed state. For purposes of peripheral attachment to the inner surface of pouch wall 13, the dome 25 has a peripheral flange 25a spaced outwardly from the periphery of filter 20.

The hollow dome may be formed of any soft, flexible, easily-deformable but shape-recoverable polymeric material such as low-density polyethylene or polyvinyl chloride, but it is believed a thermoplastic material having substantial elastomeric properties such as polyurethane is particularly suitable.

Figure 2:
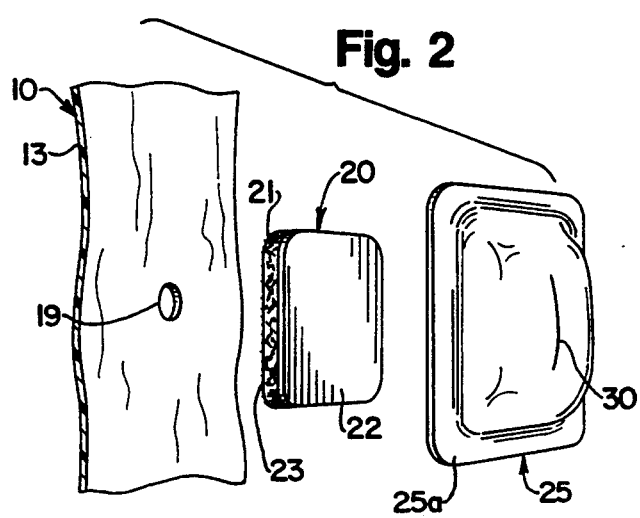
FIG. 2 is an exploded perspective view showing the relationship of the valve, deodorizing filter, and pouch wall.

As shown most clearly in FIG. 2, the dome 25 is provided with an elongated linear slit 30. The slit is formed by a cutting or slicing operation that produces smooth opposing edges without the removal or extraction of plastic material from the dome. Therefore, when the dome is in its normal untensioned or undeformed state, the opposing edges 30a, 30b that define the slit are in sealing engagement with each other. However, when squeezing or pinching forces are exerted on the dome from opposite ends of the slit in the general directions indicated by the arrows in FIG. 3, the edges 30a, 30b spread apart. The direction of squeezing forces need not be in precise alignment with the slit in order to cause the edges of the slit to buckle and spread. As illustrated in FIG. 4, squeezing forces applied to the rounded corners of the generally rectangular dome will also cause edges 30a, 30b to separate.

The dome therefore functions as a normally-closed relief valve that may be easily opened by the application of squeezing force from generally opposite ends of the slit when venting of gases from the pouch is desired. Controllable venting would be achieved even if filter 20 were absent but, in the preferred embodiment depicted in the drawings, the deformable plastic dome also performs the important function of protecting a filter from contact with the liquid and solid contents of the pouch, thereby protecting the filter from becoming clogged and inoperative. The dome-shaped manually-operable relief valve therefore extends the effective life of the filter media and also allows the user to select the time and place when venting of the pouch occurs.

Figure 3:
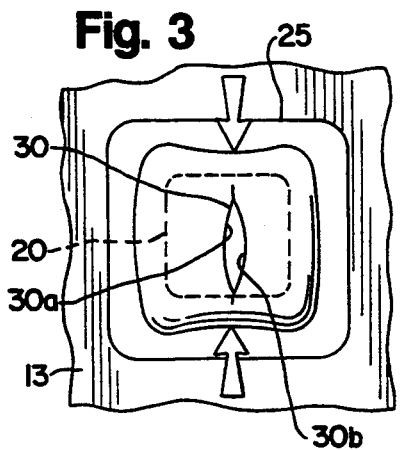
FIG. 3 is a fragmentary elevational view illustrating how the normally-closed valve may be opened.
Figure 4:
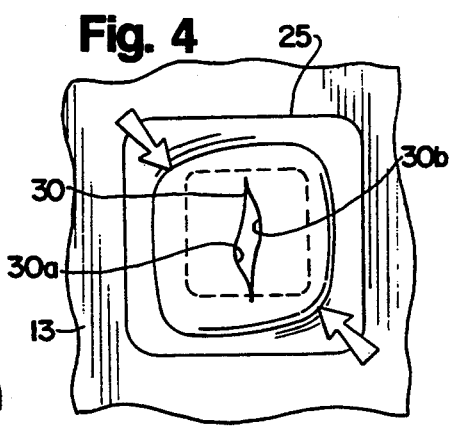
FIG. 4 is an elevational view similar to FIG. 3 also showing how the vent valve may be opened.

It is believed apparent that while FIGS. 3 and 4 show squeezing forces being applied directly to the dome, such forces are actually transmitted through the thin flexible wall of the pouch. Applying squeezing forces to the outer surface of pouch wall 13 from opposite sides of the dome, a user may easily cause the deformation that opens the relief valve and permits venting of the pouch.

Figure 5:
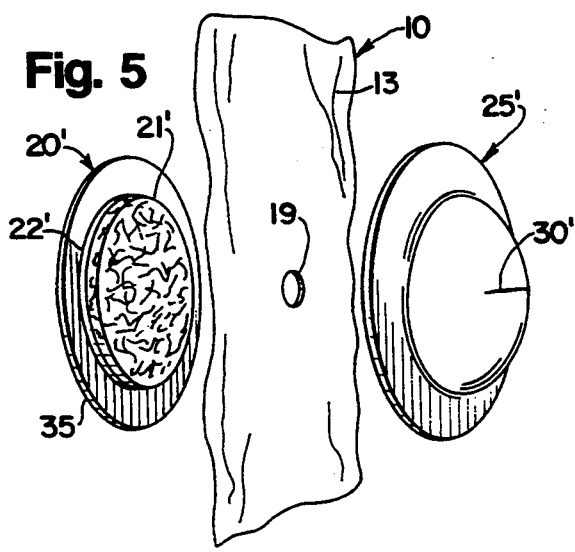
FIG. 5 is an exploded perspective view depicting a second embodiment of the invention.
Figure 6:
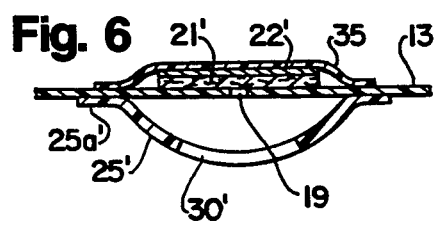
FIG. 6 is a horizontal fragmentary sectional view showing the components of the second embodiment in assembled condition.
Figure 7:
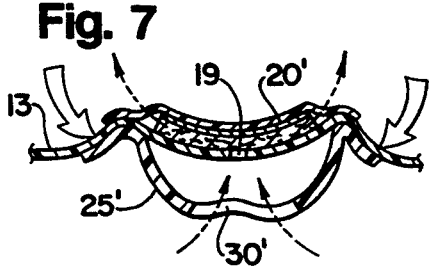
FIG. 7 is a horizontal sectional view similar to FIG. 6 but illustrating the application of forces for opening the valve.

In the embodiment depicted in FIGS. 5–7, the deformable, shape-recoverable dome 25' is circular than rather than rectangular in outline and the filter 20' is also circular and is located externally of the pouch. The filter pad or disc 21' extends over and about vent opening 19 on the outside of pouch wall 13 and is held in place by a porous or gas-transmissible cover 35 that is preferably formed of thermoplastic material and heat sealed or otherwise securely affixed to the pouch wall about the periphery of filter pad 21'. If flow of gas through the filter is to be limited to a generally radial direction, as opposed to axial flow, then the outer surface of the pad or disc 21' may be covered by a gas-impermeable film or covering 22'. Preferably, the surface of the filter pad 21' facing pouch wall 13 is adhesively secured to that wall or is held in contact with the outer surface of that wall by other suitable means.

The linear slit 30' of the dome-shaped relief valve 25' is opened by squeezing forces applied in the same manner as described in connection with the first embodiment. FIG. 6 depicts the dome-shaped relief valve in its undeformed and normally closed state, whereas FIG. 7 illustrates the application of squeezing forces that result in dome deformation and venting of the pouch. When the dome-shaped valve is in its normally-closed state, the solid and liquid contents of the pouch cannot reach vent opening 19 and cause clogging of that opening and of the filter secured to the pouch wall about that opening.

In the embodiment of FIGS. 5-7, the filter is externally mounted but it will be understood that, if desired, the filter may be located within the pouch in the same manner shown and described in connection with the embodiment of FIGS. 1-4. Conversely, the embodiment of FIGS. 1-4 may be provided with an externally-mounted filter. In either case, the deformable relief valve 30, 30' is located within the pouch, prevents the venting of gases unless a squeezing force is applied, and protects the filter from exposure to effluent that might clog the filter and render it inoperative.

It will be noted that the slit 30 extends vertically, that is, in a longitudinal direction relative to the vertically-elongated pouch 10, whereas slit 30' is oriented horizontally or transversely with respect to the pouch. Either orientation is suitable, but it is preferred that the slit not extend at an angle other than vertical or horizontal for ease of operation, bearing in mind that to open the valve a user must apply squeezing forces in prescribed directions from generally opposite ends of the slit.

While, in the foregoing, I have disclosed embodiments of the invention in considerable detail for purposes of illustration, it will be understood by those skilled in the art that many of these details may be varied without departing from the spirit and scope of the invention.

I claim:

1. An ostomy pouch having a pair of thin flexible side walls and having a stoma-receiving opening; a vent opening in one of said walls for the discharge of gases from said pouch; and normally-closed valve means for normally blocking the escape of gases accumulating in said pouch; said value means comprising a flexible, shape-recovering plastic dome located within said pouch and secured to said one wall over said vent opening; said dome being provided with linear slit having opposing edges normally in sealing engagement with each other to prevent the escape of gases from said pouch but being spread apart to permit such escape when said dome is squeezed between the fingers in directions inwardly from generally opposite ends of said slit.

2. The pouch of claim 1 in which a deodorizing filter extends across said vent opening for filtering and deodorizing gases vented from said pouch.

3. The pouch of claim 2 in which said filter is an internal filter located in said pouch within said dome.

4. The pouch of claim 3 in which said filter is secured to an inner surface portion of said one wall about said vent opening.

5. The pouch of claim 2 in which said filter is an external filter secured to an outer surface portion of said one wall about said vent opening.

6. The pouch of claims 1 or 2 in which said slit extends generally vertically when said pouch is worn.

7. The pouch of claims 1 or 2 in which said slit extends generally horizontally when said pouch is worn.

8. The pouch of claims 1 or 2 in which said pouch is elongated and said slit extends in a direction generally lengthwise of said pouch.

9. The pouch of claims 1 or 2 in which said pouch is elongated and said slit extends in a direction generally transversely with respect to said pouch.

10. The pouch of claims 1 or 2 in which said dome is generally rectangular in outline.

11. The pouch of claims 1 or 2 in which said dome is generally circular in outline.

12. An ostomy pouch having a pair of thin, flexible side walls and having a stoma-receiving opening; adhesive means for securing said pouch to a body wall of a wearer with said opening in register with the wearer's stoma; a vent opening in one of said walls for the discharge of gases from said pouch; a filter disc secured to said one wall of said pouch about said vent opening for filtering gases flowing therethrough; and normally-closed valve means for normally blocking the escape of gases accumulating in said pouch; said valve means comprising a flexible, shape-recovering plastic dome located within said pouch and having edge portions sealingly secured to said one wall about said vent opening; said dome being provided with a linear slit having opposing edges normally in sealing engagement with each other for restraining solid and liquid matter in said pouch from contacting said filter and for preventing the escape of gases through said vent as such gases accumulate in said pouch; said dome being deformable when squeezed between the fingers in directions inwardly from generally opposite ends of said slit to cause said edges to spread apart and allow the flow of accumulated gases from said pouch through said filter and vent opening.

13. The pouch of claim 12 in which said filter is an internal filter located in said pouch within said dome.

14. The pouch of claim 13 in which said filter is secured to an inner surface portion of said one wall about said vent opening.

15. The pouch of claim 12 in which said filter is an external filter secured to an outer surface portion of said one wall about said vent opening.

16. The pouch of claim 12 in which said slit extends generally vertically when said pouch is worn.

17. The pouch of claim 12 in which said slit extends generally horizontally when said pouch is worn.

18. The pouch of claim 12 in which said dome is generally rectangular in outline.

19. The pouch of claim 12 in which said dome is generally circular in outline.

* * * * *